United States Patent

Hendi

Patent Number: 6,057,449

Date of Patent: May 2, 2000

[54] DIRECT PREPARATION OF PYRROLO[3,4-C]PYRROLES

[75] Inventor: Shivakumar B. Hendi, Newark, Del.

[73] Assignee: Ciba Specialty Chemicals Corporation, Tarrytown, N.Y.

[21] Appl. No.: 09/311,094

[22] Filed: May 13, 1999

Related U.S. Application Data

[60] Provisional application No. 60/087,773, Jun. 2, 1998.

[51] Int. Cl.⁷ .............. C07D 487/02; C07D 403/14
[52] U.S. Cl. .................. 546/276.7; 548/453
[58] Field of Search .............. 548/453; 546/276.7

[56] References Cited

U.S. PATENT DOCUMENTS

| | | | |
|---|---|---|---|
| 4,362,704 | 12/1982 | Taylor et al. | 423/150 |
| 4,579,949 | 4/1986 | Rochat et al. | 546/167 |
| 4,720,305 | 1/1988 | Iqbal et al. | 106/288 |
| 4,778,899 | 10/1988 | Pfenninger et al. | 548/453 |
| 4,791,204 | 12/1988 | Jost et al. | 548/101 |
| 4,810,304 | 3/1989 | Jaffe et al. | 106/494 |
| 4,931,566 | 6/1990 | Surber et al. | 548/453 |
| 4,992,101 | 2/1991 | Jaffe et al. | 106/498 |
| 5,200,528 | 4/1993 | Wooden et al. | 548/453 |
| 5,264,032 | 11/1993 | Dietz et al. | 106/411 |
| 5,424,429 | 6/1995 | Hendi et al. | 546/49 |
| 5,457,203 | 10/1995 | Hendi et al. | 546/56 |
| 5,476,949 | 12/1995 | Wallquist et al. | 548/453 |
| 5,492,564 | 2/1996 | Wooden et al. | 106/493 |
| 5,502,208 | 3/1996 | Wallquist | 548/453 |
| 5,827,364 | 10/1998 | Hendi | 106/495 |
| 5,871,575 | 2/1999 | Ruch et al. | 106/498 |
| 5,973,146 | 10/1999 | Rochat et al. | 544/144 |

FOREIGN PATENT DOCUMENTS

| | | |
|---|---|---|
| 0 485 337 | 5/1992 | European Pat. Off. . |
| 0 643 110 | 3/1995 | European Pat. Off. . |
| 0 811 625 | 12/1997 | European Pat. Off. . |
| 2 238 550 | 6/1991 | United Kingdom . |

Primary Examiner—Joseph McKane
Assistant Examiner—Sonya Wright
Attorney, Agent, or Firm—David R. Crichton

[57] ABSTRACT

A process is disclosed for the direct preparation of pigmentary 1,4-diketopyrrolo-[3,4-c]pyrroles of the formula (I)

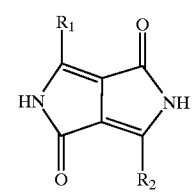

(I)

wherein each of $R_1$ and $R_2$ independently of the other is an isocyclic or heterocyclic aromatic radical, which process comprises heating an appropriate molar ratio of a disuccinate with a nitrile of the formula (II)

$$R_1\text{—CN} \qquad (II)$$

or of the formula (III)

$$R_2\text{—CN} \qquad (III)$$

or with mixtures of said nitrites, in an organic solvent and in the presence of a strong base and an effective amount of a selected particle growth inhibitor of formula (IV)–(X), and then obtaining the compound of formula (I) from the reaction product by protolysis. The process yields pigmentary 1,4-diketopyrrolo-[3,4-c]pyrroles directly, i.e., without the need for additional particle-size reducing aftertreatments. Also disclosed is a composition comprising a pigmentary 1,4-diketopyrrolo-[3,4-c]pyrrole and the particle growth inhibitor. These pigment compositions are useful for pigmenting high molecular weight organic materials.

25 Claims, No Drawings

DIRECT PREPARATION OF PYRROLO[3,4-C]PYRROLES

This application claims the benefit of U.S. Provisional Application No. 60/087,773, filed Jun. 2, 1998.

BACKGROUND

The diketopyrrolopyrrole family of compounds and their pigmentary properties are well known. The pigmentary diketopyrrolopyrroles include unsubstituted 1,4-diketopyrrolopyrrole as well as various substituted diketopyrrolopyrroles, including those substituted by isocyclic or heterocyclic aromatic radicals. They are suitable for pigmenting organic materials of high molecular weight.

It is known in the pigments art that substituted diketopyrrolopyrrole pigments can be prepared by the reaction of a mole of a disuccinate with two moles of an aromatic nitrile or one mole each of two different aromatic nitriles. U.S. Pat. No. 4,579,949 describes reaction of a disuccinate with aromatic nitriles in an organic solvent and in the presence of a strong base at elevated temperature, and subsequently protolyzing the resultant salt. The product of such process, known as crude diketopyrrolopyrrole, generally has a medium to large particle size, which size has been shown to be unsuitable for certain end uses, such as in automotive coatings, requiring a high degree of transparency. Many automotive styles with metallic-effects are created by the use of a combination of aluminum or mica flakes and uniformly small particle size pigments. It therefore becomes necessary to further process the larger particle size crude pigments to develop the requisite pigmentary properties, such as smaller particle size, particle shape, polymorphic phase and tinctorial strength.

Particle size manipulation has thus become a significant art in pigment technology. Highly desirable pigments are traditionally produced by subjecting the crude pigments to a variety of pigment finishing methods, also called pigment conditioning steps, the purpose of which is to create pigments of defined particle size with a narrower particle size distribution, preferably in a single homogeneous crystal phase. In the case of diketopyrrolopyrroles, the crude form is commonly convened to a useable pigmentary form by milling it with large quantities of inorganic salt followed by extraction of the resulting mill powder, or by dissolving the pigment in large quantities of sulfuric acid and drowning the solution in water (known as acid pasting). These multistep procedures generally require a diversity of operations conducted at elevated temperatures in acidic environments; therefore, simpler and more economical procedures for preparing pigmentary diketopyrrolopyrroles are highly desired in the industry.

Work has been carried out in the art to prepare smaller particulate forms of diketopyrrolopyrrole pigments. For example, U.S. Pat. No. 5,502,208 relates that certain cyano-substituted diketopyrrolopyrrole pigments can be prepared in finely particulate form by carrying out the protonation step in water and/or an alcohol in the presence of an acid in an amount sufficient to keep the pH less than 9, and a temperature of greater than 90° C. Inclusion of particle growth inhibitors during the synthesis of diketopyrrolopyrroles is not mentioned.

It is known from U.S. Pat. Nos. 5,457,203 and 5,424,429 that certain phthalimidomethylquinacridone compounds are useful as a growth inhibitor in the oxidation reaction of a dihydroquinacridone to form a quinacridone. The conversion of dihydroquinacridone to quinacridone is performed using a mild oxidizing agent in an alkaline alcoholic medium. It is proposed that under these oxidation conditions the phthalimidomethyl quinacridone partially ring opens to an alkali metal salt of the carboxy carbonamide.

It is, however, surprising that the synthesis of a diketopyrrolopyrrole proceeds smoothly in the presence of phthalimidomethylquinacridone to generate a uniformly small particle size pigment. The phthalimidomethylquinacridone molecule, which is structurally and chemically dissimilar to a diketopyrrolopyrrole, unexpectedly acts as a particle size adjusting template for the diketopyrrolopyrrole. Also surprisingly, the phthalimidomethylquinacridone derivative has no detrimental effect on either the color saturation or the chemical yield of the synthesized diketopyrrolopyrrole pigment. While the conversion of dihydroquinacridone to quinacridone, as described in U.S. Pat. Nos. 5,457,203 and 5,424,429, involves only aromatization of the pentacyclic heterocycle, in the case of diketopyrrolopyrroles, the addition of the dienolate of the succinate to aromatic nitrites involves intramolecular ring closure. The reaction mechanisms for the synthesis of the two types of pigments are entirely different.

The primary object of the present invention is to prepare useful pigmentary diketopyrrolopyrroles directly during synthesis, without the need for particle size reducing after-treatments. The synthetic method of the present invention is highly desirable as it avoids multistep pigment finishing procedures which create a burden on the environment. Further, this route to the synthesis of small particle size pigments, when adding growth inhibitors during the addition of nitrites to the succinate in the presence of a strong deprotonating agent, is of great economic significance. Other objects will become apparent upon reference to the more detailed description.

BRIEF SUMMARY OF THE INVENTION

It has been discovered that 1,4-diketopyrrolo[3,4-c] pyrroles of pigmentary quality and desirable crystallinity and crystal phase can be prepared directly, without the need for further particle size reducing after treatments, by carrying out the addition of the dienolate of the succinate to the aromatic nitrites in the presence of a specified particle growth inhibitor. A wide variety of diketopyrrolopyrrole pigments with different particle sizes and specific areas, and thus, varying transparency/opacity can be prepared by using appropriate amounts of a particle growth inhibitor.

The particle size of the 1,4-diketopyrrolo[3,4-c]pyrroles of formula (I) is inversely proportional to the amount of the growth inhibiting agent present during the reaction of the nitrile with the disuccinate. Thus, a smaller particle size 1,4-diketopyrrolo[3,4-c]pyrrole product is obtained when more particle growth inhibitor is added to the reaction mixture.

The present process provides an improvement in simplicity and economy for the preparation of a variety of small particle size diketopyrrolopyrrole pigments. According to the invention, the direct preparation of pigmentary diketopyrrolopyrroles is accomplished simply by performing the addition of the dienolate of the succinate to the aromatic nitrile by known methods, but in the presence of an appropriate amount of a specified growth inhibitor. This approach eliminates the need for laborious, multistep manufacturing finishing processes which are currently practiced in the pigments industry for the manufacture of diketopyrrolo[3,4-c]pyrrole pigments.

DETAILED DESCRIPTION

The present invention relates to a process for the direct preparation of 1,4-diketopyrrolo[3,4-c]pyrroles of the formula (I)

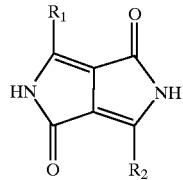
(I)

wherein each of $R_1$ and $R_2$ independently of the other is an isocyclic or heterocyclic aromatic radical, which process comprises heating an appropriate molar ratio of a disuccinate with a nitrile of the formula (II)

(II)

or of the formula (III)

(III)

or with mixtures of said nitriles, in an organic solvent and in the presence of a strong base and an effective amount of a particle growth inhibitor, to form an intermediate condensation product, and then protolyzing said intermediate condensation product to form the compound of formula (I), wherein said particle growth inhibitor is a compound of formula (IV)

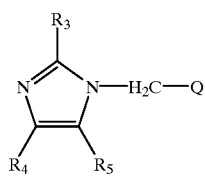
(IV)

wherein $R_3$, $R_4$ and $R_5$ are, each independently of the other, hydrogen, chlorine, bromine, fluorine, $C_1$–$C_6$alkyl, $C_1$–$C_6$alkoxy or an isocyclic or heterocyclic aromatic radical and Q is a quinacridone or diketopyrrolopyrrole moiety;

a compound of formula (V)

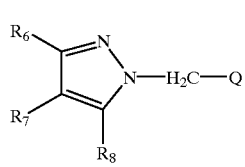
(V)

wherein $R_6$, $R_7$ and $R_8$ are, each independently of the other, hydrogen, chlorine, bromine, fluorine, $C_1$–$C_6$alkyl, $C_1$–$C_6$alkoxy or an isocyclic or heterocyclic aromatic radical and Q is as defined above;

a compound of formula (VI)

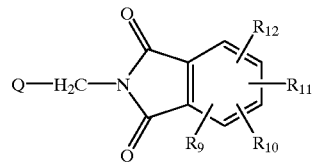
(VI)

wherein $R_9$, $R_{10}$, $R_{11}$ and $R_{12}$ are, each independently of the other, hydrogen, chlorine, bromine, fluorine, $C_1$–$C_6$alkyl, $C_1$–$C_6$alkoxy or an isocyclic or heterocyclic aromatic radical and Q is as defined above;

a compound of formula (VII)

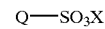
(VII)

wherein X is hydrogen, sodium, potassium, magnesium, calcium, strontium or aluminum and Q is as defined above;

a compound of formula (VII)

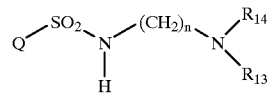
(VIII)

wherein n is an integer from 2 to 4; $R_{13}$ and $R_{14}$ are, each independently of the other, $C_1$–$C_6$alkyl or together with the nitrogen atom to which they are bonded form a 5- or 6-membered heterocyclic ring; and Q is as defined above;

a compound of formula (IX)

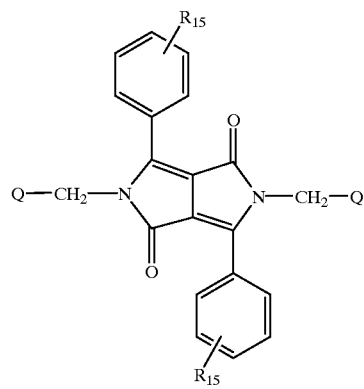
(IX)

wherein $R_{15}$ is hydrogen, chlorine, bromine, fluorine, $C_1$–$C_6$alkyl, $C_1$–$C_6$alkoxy, phenyl, di-$C_1$–$C_6$alkylamino, $C_1$–$C_6$alkylthio, phenylthio or phenoxy, and Q is as defined above; wherein said compound is substituted by from 0 to 6 moles of —SO₃M per mole of said compound, wherein M is hydrogen or a metal or ammonium cation; or a compound of the formula (X)

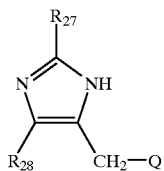

(X)

wherein R$_{27}$ and R$_{28}$ are, each independently of the other, hydrogen, chlorine, bromine, fluorine, C$_1$–C$_6$alkyl, C$_1$–C$_6$alkoxy or an isocyclic or heterocyclic aromatic radical and Q is as defined above.

The expressions "direct" or "directly", when used herein to describe a preparatory process for a pigmentary product, means that the specific surface area of the pigmentary product will be within the range which makes it suitable for use as a pigment, without additional particle size reducing aftertreatments.

The radicals R$_1$ and R$_2$ may be the same or different, but are preferably identical. R$_1$ and R$_2$ as isocyclic aromatic radicals are preferably monocyclic to tetracyclic radicals, most preferably monocyclic or bicyclic radicals such as phenyl, diphenyl, naphthyl and the like. Heterocyclic aromatic radicals R$_1$ and R$_2$ are preferably monocyclic to tricyclic radicals. These radicals may be entirely heterocyclic or may contain a heterocyclic ring and one or more fused benzene rings, and the cyano group can be linked both to the heterocyclic and to the isocyclic moiety respectively. Examples of heterocyclic aromatic radicals are pyridyl, pyrimidyl, pyrazinyl, triazinyl, furyl, pyrrolyl, thiophenyl, quinolyl, cumarinyl, benzfuranyl, benzimidazolyl, benzoxazolyl, dibenzfuranyl, benzothiophenyl, dibenzothiophenyl, indolyl, carbazolyl, pyrazolyl, imidazolyl, oxazolyl, isoxazolyl, thiazolyl, indazolyl, benzthiazolyl, pyridazinyl, cinnolyl, quinazolyl, quinoxalyl, phthalazinyl, phthalazindionyl, phthalamidyl, chromonyl, naphtholactamyl, quinolonyl, ortho-sulfobenzimidyl, maleinimidyl, naphtharidinyl, benzimidazolonyl, benzoxazolonyl, benzthiazolonyl, benzthiazothionyl, quinazolonyl, quinoxalonyl, phthalazonyl, dioxopyrimidinyl, pyridonyl, isoquinolonyl, isoquinolinyl, isothiazolyl, benzisoxazolyl, benzisothiazolyl, indazolonyl, acridonyl, quinazolindionyl, quinoxalindionyl, benzoxazindionyl, benzoxazinonyl and naphthalimidyl. Both the isocyclic and the heterocyclic aromatic radicals may contain the customary non-watersolubilising substituents such as those described below:

(1) Halogen atoms, for example, chlorine, bromine or fluorine atoms.

(2) Branched or unbranched alkyl groups containing preferably 1 to 18, especially 1 to 12, more particularly 1 to 8 and, most preferably, 1 to 4, carbon atoms. These alkyl groups may in turn contain non-watersolubilising substituents such as fluorine, hydroxyl, cyano, —OCOR$_{16}$, —OR$_{17}$, —COOR$_{16}$, —CONR$_{17}$R$_{18}$ or —R$_{16}$—OCONHR$_{16}$, wherein R$_{16}$ is alkyl, aryl such as naphthyl or benzyl or benzyl substituted by halogen, alkyl or —O-alkyl, or is a heterocyclic radical. R$_{17}$ and R$_{18}$, are, each independently of the other, hydrogen, alkyl or alkyl substituted by cyano or hydroxy, or is C$_5$–C$_6$cycloalkyl, aryl or heteroaryl, especially phenyl or phenyl substituted by halogen, alkyl or —O-alkyl, or wherein R$_{17}$ and R$_{18}$ together with the nitrogen atom form a 5- or 6-membered heterocyclic ring, for example, a morpholine, piperidine or phthalimide ring. Further possible substituents at the alkyl groups are mono- or dialkylated amino groups, aryl radicals such as naphthyl or preferably phenyl or phenyl substituted by halogen, alkyl or —O-alkyl, or also heterocyclic aromatic radicals such as 2-thienyl, 2-benzoxazolyl, 2-benzthiazolyl, 2-benzimidazolyl, 6-benzimidazolonyl, 2-, 3- or 4-pyridyl, or 2-, 4- or 6-quinolyl radicals.

If the substituents specified in (2) above in turn contain alkyl, then this alkyl may be branched or unbranched and contain preferably 1 to 18, especially 1 to 12, more particularly 1 to 8 and, most preferably, 1 to 4 carbon atoms.

Examples of unsubstituted or substituted alkyl groups are methyl, ethyl, n-propyl, isopropyl, n-butyl, sec-butyl, tert-butyl, tert-amyl, n-pentyl, n-hexyl, 1,1,3,3-tetramethylbutyl, n-heptyl, n-octyl, nonyl, decyl, undecyl, dodecyl, hydroxymethyl, trifluoromethyl, trifluoroethyl, cyanomethyl, methoxycarbonylmethyl, acetoxymethyl or benzyl.

(3) The —OR$_{19}$ group, wherein R$_{19}$ is hydrogen, alkyl or aryl such as naphthyl or preferably phenyl or phenyl substituted by halogen, alkyl or —O-alkyl, or is C$_5$–C$_6$cycloalkyl, aralkyl or a heterocyclic radical. In the definition of R$_{19}$, alkyl may contain a number of carbon atoms as specified as preferred in (2) above. Typical examples of R$_{19}$ are methyl, ethyl, n-propyl, isopropyl, trifluoroethyl, phenyl, o-, m- or p-chlorophenyl, o-, m- or p-methylphenyl, alpha- or beta-naphthyl, cyclohexyl, benzyl, thienyl or pyranylmethyl.

(4) The —SR$_{19}$ group, wherein R$_{19}$ is as defined in (3) above. Typical examples of R$_{19}$ are methyl, ethyl, n-propyl, isopropyl, phenyl, o-, m- or p-chlorophenyl, o-, m- or p-methylphenyl, alpha- or beta-naphthyl, cyclohexyl, benzyl, thienyl or pyranylmethyl.

(5) The cyano group.

(6) The group of the formula —NR$_{17}$R$_{18}$, wherein R$_{17}$ and R$_{18}$ are as defined in (2) above. Typical examples are amino, methylamino, dimethylamino, ethylamino, diethylamino, isopropylamino, beta-hydroxyethylamino, beta-hydroxypropylamino, N,N-bis-(beta-hydroxyethyl) amino, N,N-bis-(beta-cyanoethyl)amino, cyclohexylamino, phenylamino, N-methylphenylamino, benzylamino, dibenzylamino, piperidyl or morpholyl.

(7) The group of the formula —COOR$_{16}$, wherein R$_{16}$ is as defined in (2) above. Examples of R$_{16}$ are methyl, ethyl, isopropyl, tert-butyl, n-butyl, phenyl, benzyl or furfuryl.

(8) The group of the formula —COR$_{19}$ wherein R$_{19}$ is defined as in (3) above. Examples of R$_{19}$ are methyl, ethyl, tert-butyl, phenyl, o-, m- or p-chlorophenyl, o-, m- or p-methylphenyl or alpha- or beta-naphthyl.

(9) The group of the formula —NR$_{20}$COR$_{16}$, wherein R$_{16}$ is as defined as in (2) above. R$_{20}$ is hydrogen, alkyl, aryl, for example naphthyl or preferably phenyl or phenyl substituted by halogen, alkyl or —O-alkyl, or is C$_5$–C$_6$cycloalkyl, aralkyl or the radical —COR$_{16}$, whilst two radicals —COR$_{16}$ together with the nitrogen atom are able to form a heterocyclic ring. In the definition of R$_{20}$, alkyl may contain a number of carbon atoms as specified as preferred in (2) above. Typical examples are acetylamino, propionylamino, butyrylamino, benzoylamino, p-chlorobenzoylamino, p-methylbenzoylamino, N-methylacetylamine, N-methylbenzoylamino, N-succinimido or N-phthalimidio.

(10) The group of the formula —NR$_{19}$COOR$_{16}$, wherein R$_{16}$ and R$_{19}$ are as defined in (2) and (3) above, respectively.

Typical examples are the —NHCOOCH$_3$, NHCOOC$_2$H$_5$ or NHCOOC$_5$H$_5$ groups.

(11) The group of the formula —NR$_{19}$CONR$_{17}$R$_{18}$, wherein R$_{19}$, R$_{17}$ and R$_{18}$ are as defined in (3) and (2) above. Typical examples are ureido, N-methylureido, N-phenylureido or N,N'-2',4'-dimethylphenylureido.

(12) The group of the formula —NHSO$_2$R$_{16}$, wherein R$_{16}$ is as defined as in (2) above. Typical examples are methanesulfonylamino, phenylsulfonylamino, p-toluylsulfonylamino or beta-naphthylsulfonylamino.

(13) The groups of the formula —SO$_2$R$_{16}$ or —SOR$_{16}$, wherein R$_{16}$ is as defined in (2) above. Typical examples are methylsulfonyl, ethylsulfonyl, phenylsulfonyl, 2-naphthylsulfonyl, phenylsulfoxidyl.

(14) The group of the formula —SO$_2$OR$_{16}$, wherein R$_{16}$ is as defined in (2) above. Typical examples of R$_{16}$ are methyl, ethyl, phenyl, o-, m- or p-chlorophenyl, o-, m- or p-methylphenyl, alpha- or beta-naphthyl.

(15) The group of the formula —CONR$_{17}$R$_{18}$, wherein R$_{17}$ and R$_{18}$ are as defined in (2) above. Examples of R$_{17}$ and R$_{18}$ are carbonyl, N-methylcarbamoyl, N-ethylcarbamoyl, N-phenylcarbamoyl, N,N-dimethylcarbamoyl, N-methyl-N-phenylcarbamoyl, N-alpha-N-naphthylcarbamoyl or N-piperidylcarbamoyl.

(16) The group of the formula —SO$_2$NR$_{17}$R$_{18}$, wherein R$_{17}$ and R$_{18}$ are as defined in (2) above. Typical examples are sulfamoyl, N-methylsulfamoyl, N-ethylsulfamoyl,

(17) The group of the formula —N═NR$_{21}$, wherein R$_{21}$ is the radical of a coupling component or is a phenyl radical which is unsubstituted or substituted by halogen, alkyl or O-alkyl. In the definition of R$_{21}$, alkyl may contain a number of carbon atoms as specified in (2) as preferred above. Examples of R$_{21}$ are acetoacetarylide, pyrazolyl, pyridonyl, o- or p-hydroxyphenyl, o-hydroxynaphthyl, p-aminophenyl or p-N,N-dimethylaminophenyl radicals.

(18) The group of the formula —OCOR$_{16}$, wherein R$_{16}$ is as defined in (2) above. Examples of R$_{16}$ are methyl, ethyl, phenyl, o-, m- or p-chlorophenyl.

(19) The group of the formula —OCONHR$_{16}$, wherein R$_{16}$ is as defined in (2) above. Examples of R$_{16}$ are methyl, ethyl, phenyl, o-, m- or p-chlorophenyl.

The preferred starting material employed in the preparation of compounds of the formula (I) according to this invention is a homogeneous nitrile of the formula (II) or (III). It is also preferred to use nitrites of the formula (II) and/or (III), wherein R$_1$ and R$_2$ are unsubstituted phenyl or naphthyl or which phenyl or naphthyl contain non-watersolubilising substituents.

In particular, the starting materials employed are nitrites of the formula (XI)

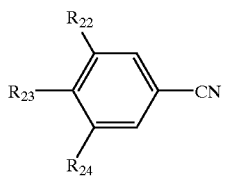

(XI)

wherein each of R$_{22}$, R$_{23}$ and R$_{24}$, independently of one another, is hydrogen, fluorine, chlorine, bromine, carbamoyl, cyano, trifluoromethyl, C$_2$–C$_{13}$alkylcarbamoyl, C$_1$–C$_{12}$alkyl, C$_1$–C$_{12}$alkoxy, C$_1$–C$_{12}$alkylmercapto, C$_2$–C$_{13}$alkoxycarbonyl, C$_2$–C$_{13}$alkanoylamino, C$_1$–C$_{12}$monoalkylamino, C$_2$–C$_{24}$dialkylamino, phenyl or phenoxy, phenylmercapto, phenoxycarbonyl, phenylcar-bamoyl or benzoylamino, each unsubstituted or substituted by halogen, C$_1$–C$_{12}$alkyl or C$_1$–C$_{12}$alkoxy, with the proviso that at least one of R$_{22}$, R$_{23}$ or R$_{24}$ is hydrogen.

Most preferably, the starting materials employed are nitriles of the formula (XII)

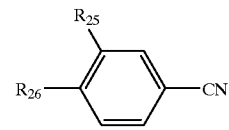

(XII)

wherein both R$_{25}$ and R$_{26}$ are hydrogen, or one of R$_{25}$ or R$_{26}$ is chlorine, bromine, C$_1$–C$_4$alkyl, cyano, C$_1$–C$_4$alkoxy, or is phenyl, phenoxy, carbamoyl or C$_2$–C$_5$alkylcarbamoyl, each unsubstituted or substituted by chlorine or methyl, or is phenylcarbamoyl which is unsubstituted or substituted by chlorine, methyl or methoxy, and the other is hydrogen.

The disuccinates to be used in the process according to the invention include dialkyl, diaryl or monoalkyl-monoaryl succinates. The dialkyl and diaryl succinates may also be asymmetrical. However, it is preferred to use symmetrical disuccinates, most preferably symmetrical dialkyl succinates, most preferably symmetrical dialkyl succinates. If a diaryl or monoaryl-monoalkyl succinate is employed, aryl denotes preferably phenyl which is unsubstituted or substituted by halogen such as chlorine, C$_1$–C$_6$alkyl such as ethyl, methyl, isopropyl or tert-butyl, or C$_1$–C$_6$alkoxy such as methoxy or ethoxy. The preferred meaning of aryl is unsubstituted phenyl. If a dialkyl or monoalkyl-monoaryl succinate is employed, then alkyl may be unbranched or branched, preferably branched, and may contain preferably 1 to 18, in particular 1 to 12, more particularly 1 to 8 and more preferably 1 to 5, carbon atoms. Branched alkyl is preferably sec- or tert-alkyl, for example, isopropyl, sec-butyl, tert-butyl, tert-amyl and cyclohexyl.

Examples of disuccinates are dimethyl succinate, diethyl succinate, dipropyl succinate, dibutyl succinate, dipentyl succinate, dihexyl succinate, diheptyl succinate, dioctyl succinate, diisopropyl succinate, di-sec-butyl succinate, di-tert-butyl succinate, di-tert-amyl succinate, di-[1,1-dimethylbutyl]succinate, di-[1,1,3,3-tetramethylbutyl] succinate, di-[1,1-dimethylpentyl]succinate, di-[1-methyl-ethylbutyl]succinate, di-[1,1-diethylpropyl]succinate, diphenyl succinate, di-[4-methylphenyl]succinate, di-[4-chlorophenyl]succinate, monoethyl-monophenyl succinate, and dicyclohexyl succinate. Most preferably, the starting disuccinate is diisopropyldisuccinate.

The disuccinates and the nitriles of formula (II) or (III) are known compounds and may be prepared by known methods.

It is advantageous to use the nitrile to be reacted with the disuccinate in more than only stoichiometric proportions. It has been found that the yield of final product may be improved by using an excess of nitrile over disuccinate, in which case the optimum amount must be determined according to the respective reactants and may be up to ten times the stoichiometric amount required with respect to the disuccinate. It is normally possible to recover excess nitrile. An excess of disuccinate over the nitrile can often have a positive influence on the yield, in which case the excess may be up to twice the stoichiometrically required amount of disuccinate.

The reaction of the disuccinate with the nitrile is carried out in an organic solvent. Examples of suitable solvents are primary, secondary or tertiary alcohols containing 1 to 10 carbon atoms, for example, methanol, ethanol, n-propanol, isopropanol, n-butanol, sec-butanol, tert-butanol, n-pentanol, 2-methyl-2-butanol, 2-methyl-2-pentanol, 3-methyl-3-pentanol, 2-methyl-2-hexanol, 3-ethyl-3-pentaol, 2,4,4-trimethyl-2-pentanol, or glycols such as ethylene glycol or diethylene glycol; and also ethers such as tetrahydrofuran or dioxan, or glycol ethers such as ethylene glycol methyl ether, ethylene glycol ethyl ether, diethylene glycol monomethyl ether or diethylene glycol monoethyl ether; as well as dipolar aprotic solvents such as acetonitrile, benzonitrile, dimethylformamide, N,N-dimethylacetamide, nitrobenzene, N-methylpyrrolidone; aliphatic or aromatic hydrocarbons such as benzene or benzene substituted by alkyl, alkoxy or halogen, for example, toluene, xylene, anisole or chlorobenzene; or aromatic heterocyclic compounds such as pyridine, picoline or quinoline. In addition, it is also possible to use the nitrile of formula (II) or (III) simultaneously as solvent if it is liquid in the temperature range in which the reaction takes place. Mixtures of the above solvents may also be used. It is convenient to use 5 to 20 parts be weight of solvent per 1 part by weight of reactants.

In the process according to the invention, it is preferred to use an alcohol as solvent, in particular a secondary or tertiary alcohol. Preferred tertiary alcohols are tert-butanol and tert-amyl alcohol. Mixtures of these preferred solvents with aromatic hydrocarbons such as toluene or xylene, or halogen-substituted benzene such as chlorobenzene, are also useful.

The process according to the invention is carried out in the presence of a strong base. Suitable strong bases are in particular the alkali metals themselves such as lithium, sodium or potassium, or alkali metal amides such as lithium amide, sodium amide or potassium amide, or alkali metal hydrides such as lithium, sodium or potassium hydride, or alkaline earth metal alcoholates or alkali metal alcoholates which are derived preferably from primary, secondary or tertiary aliphatic alcohols containing from 1 to 10 carbon atoms, for example, lithium methylate, sodium methylate or potassium methylate, or lithium, sodium or potassium ethylate, lithium, sodium or potassium n-propylate, lithium, sodium or potassium iso-propylate, lithium, sodium or potassium n-butylate, lithium, sodium or potassium sec-butylate, lithium, sodium or potassium tert-butylate, lithium, sodium or potassium 2-methyl-2-butylate, lithium, sodium or potassium 2-methyl-2-pentylate, lithium, sodium or potassium 3-methyl-3-pentylate, lithium, sodium or potassium 3-ethyl-3-pentylate or lithium, sodium or potassium 3-ethyl-3-pentylate. Additionally, a mixture of these bases may also be employed.

The preferred strong base is an alkali metal alcoholate, the alkali being preferably sodium or potassium and the alcoholate being preferably derived from a secondary or tertiary alcohol. Particularly preferred strong bases are therefore, for example, sodium or potassium isopropylate, sodium or potassium sec-butylate, sodium or potassium tert-butylate and sodium or potassium tert-amylate. Moreover, the alkali metal alcoholates may be prepared in situ by reacting the appropriate alcohol with the alkali metal, alkali metal hydride or alkali metal amide.

The strong base is employed in an amount of preferably from about 0.1 to about 10 moles, most preferably from about 1.9 to about 4.0 moles, based on one mole of the disuccinate. Although a stoichiometric amount of base may suffice, an excess of base has been found to have an advantageous effect on the yield.

The growth inhibitor is a compound of the formula (IV) to (X). The compounds of formula (IV) to (VIII) and (X) are known in the art and may be prepared by known methods. For example, the compounds of formula (IV) are prepared by reaction of an imidazole with formaldehyde to form an intermediate 1-hydroxymethylimidazole, which in turn reacts with a quinacridone to form an imidazol-1-ylmethylquinacridone. The compounds of formula (X) are prepared by reaction of a 2-hydroxymethylimidazole with quinacridone as described in U.S. Pat. No. 4,986,852, herein incorporated by reference.

Examples of suitable particle growth inhibitors of formula (IV) include imidazol-1-ylmethylquinacridone, imidazol-1-ylmethyldiketopyrrolopyrrole and the like; of formula (V) include pyrazol-1-ylmethylquinacridone, pyrazol-1-ylmethyldiketopyrrolopyrrole and the like; of formula (VI) include phthalimidomethylquinacridone, phthalimidomethyldiketopyrrolopyrrole and the like; of formula (VII) include quinacridone monosulfonic acid, aluminum quinacridone monosulfonate, diketopyrrolopyrrole monosulfonic acid, sodium diketopyrrolopyrrole monosulfonate, potassium diketopyrrolopyrrole monosulfonate, calcium diketopyrrolopyrrole monosulfonate, magnesium diketopyrrolopyrrole monosulfonate, strontium diketopyrrolopyrrole monosulfonate and the like; of formula (VIII) include dimethylaminopropyl quinacridone monosulfoamide, dimethylaminopropyl quinacridone disulfoamide and the like; and of formula (X) include imidazol-2-ylmethylquinacridone and the like.

In the compounds of formula (IV)–(X), Q is an unsubstituted or substituted quinacridone or diketopyrrolopyrrole radical. Possible substituents include halogen, $C_1$–$C_6$alkyl, $C_1$–$C_6$alkoxy, phenyl, di-$C_1$–$C_6$alkylamino, $C_1$–$C_6$alkylthio, phenylthio or phenoxy. When Q represents a quinacridone radical, it is preferably an unsubstituted quinacridone radical or a quinacridone radical which is substituted by one or more methyl, tert-butyl, phenyl or chlorine, for example 4,11-dichloroquinacridone. When Q represents a diketopyrrolopyrrole radical, it is preferably unsubstituted diketopyrrolopyrrole or diketopyrrolopyrrole which is substituted by one or more methyl, tert-butyl, phenyl or chlorine.

In the compounds of formula (IV), $R_3$, $R_4$ and $R_5$, as an isocyclic aromatic radical, may be an unsubstituted or a substituted monocyclic to tetracyclic radical, most preferably an unsubstituted or substituted monocyclic or bicyclic radical such as phenyl, diphenyl, naphthyl, 2-methylphenyl, 3-methylphenyl, 4-methylphenyl, 3-chlorophenyl, 4-chlorophenyl, 2-methoxyphenyl, 3-methoxyphenyl, 4-methoxyphenyl, 2,3-dimethylphenyl, 2,4-dimethylphenyl, 2,5-dimethylphenyl, 3,4-dimethylphenyl, 3,5-dimethylphenyl, 2,3-dichlorophenyl, 2,4-dichlorophenyl, 2,5-dichlorophenyl, 3,4-dichlorophenyl, 3,5-dichlorophenyl, 2,3-dimethoxyphenyl, 2,4-dimethoxyphenyl, 2,5-dimethoxyphenyl, 3,4-dimethoxyphenyl, 3,5-dimethoxyphenyl and the like. $R_3$, $R_4$ and $R_5$, as a heterocyclic aromatic radical, may be preferably a monocyclic to tricyclic radical such as pyridyl, pyrimidyl, pyrazinyl, triazinyl, furyl, pyrrolyl, thiophenyl, quinolyl, cumarinyl, benzfuranyl, benzimidazolyl, benzoxazolyl, dibenzfuranyl, benzothiophenyl, dibenzothiophenyl, indolyl, carbazolyl, pyrazolyl, imidazolyl, oxazolyl, isoxazolyl, thiazolyl, indazolyl, benzthiazolyl, pyridazinyl, cinnolyl, quinazolyl, quinoxalyl, phthalazinyl, phthalazindionyl, phthalamidyl, chromonyl, naphtholactamyl, quinolonyl, ortho-sulfobenzimidyl, maleinimidyl, naphtharidinyl, benzimidazolonyl, benzoxazolonyl, benzthiazolonyl, benzthiazothionyl, quinazolonyl, quinoxalonyl, phthalazonyl, dioxopyrimidinyl, pyridonyl, isoquinolonyl, isoquinolinyl, isothiazolyl, benzisoxazolyl, benzisothiazolyl, indazolonyl, acridonyl, quinazolindionyl, quinoxalindionyl, benzoxazindionyl, benzoxazinonyl and naphthalimidyl. In compounds of formula (V), $R_6$, $R_7$ and $R_8$; in the compound of the formula (VI), $R_9$, $R_{10}$, $R_{11}$ and $R_{12}$; and in the compound of formula (X), $R_{27}$ and $R_{28}$, as isocyclic and heterocyclic aromatic radicals, may be the same as defined hereinabove for $R_3$, $R_4$ and $R_5$.

In compounds of formula (IV), $R_3$, $R_4$ and $R_5$ are preferably, each independently of the other, hydrogen or methyl.

In the compounds of formula (V), $R_6$, $R_7$ and $R_8$ are preferably, each independently of the other, hydrogen or methyl.

In the compounds of formula (VI), $R_9$, $R_{10}$, $R_{11}$ and $R_{12}$ are preferably, each independently of the other, hydrogen, methyl or chlorine.

In the compounds of formula (VII), Q is preferably unsubstituted quinacridone or diketopyrrolopyrrole and X is preferably hydrogen, calcium, magnesium, aluminum or strontium.

In the compounds of formula (VIII), $R_{13}$ and $R_{14}$, as forming a 5- or 6-membered heterocyclic ring together with the nitrogen atom to which they are bonded, may be, for example, a morpholine, piperidine or phthalimide ring, and the like.

In compounds of formula (VIII), n is preferably 2 or 3 and $R_{13}$ and $R_{14}$ are preferably methyl.

In the compounds of formula (X), $R_{27}$ and $R_{28}$ are preferably, each independently of the other, hydrogen or methyl.

The quinacridone-substituted compounds of the formula (IX) are prepared by a one-pot reaction of a 1,4-diketo-3,6-diarylpyrrolo[3,4-c]pyrrole in a first step with paraformaldehyde in the presence of sulfuric acid to yield a sulfonated or non-sulfonated intermediate, which intermediate is reacted in a second step with quinacridone. U.S. application Ser. No. 08/938,656, filed Sep. 26, 1997, which is herein incorporated by reference, discloses this procedure.

The diketopyrrolopyrrole-substituted compounds of formula (IX) are prepared by a one-pot reaction of 1,4-diketo-3,6-diarylpyrrolo[3,4-c]pyrrole in a first step with paraformaldehyde in the presence of sulfuric acid to yield a sulfonated or non-sulfonated intermediate, which intermediate is reacted in a second step with a second 1,4-diketo-3,6-diarylpyrrolo[3,4-c]pyrrole. U.S. application Ser. No. 08/938,658, filed Sep. 26, 1997, which is herein incorporated by reference, discloses the foregoing procedure.

In the compounds of formula (IX), Q is preferably a radical derived from an unsubstituted quinacridone, 4,11-dichloroquinacridone, 4,11-dimethylquinacridone, unsubstituted diketopyrrolopyrrole, di-methyldiketopyrrolopyrrole, di-tert-butyldiketopyrrolopyrrole or di-chlorodiketopyrrolopyrrole.

Reduction in particle size of the 1,4-diketopyrrolo[3,4-c]pyrroles of formula (I) relative to the particle size of the uninhibited form thereof becomes noticeable with the inclusion of as little as 0.1% of the particle growth inhibitor relative to the weight of the starting nitrile. The level of the inhibitor can be as high as 10% by weight. Although the particle growth inhibitor can be present in amounts greater than 10%, using more than said amount may adversely affect the color.

A variety of pigments having varying degrees of particle size and transparency require a range of from greater than 0.1%, for example 0.2%, to about 10% of the particle growth inhibitor. A preferred range of inhibitor incorporated during the reaction of the nitrile with the disuccinate to produce the pigmentary 1,4-diketopyrrolo[3,4-c]pyrrole of formula (I) is the minimum amount necessary to directly prepare a pigmentary 1,4-diketopyrrolo[3,4-c]pyrrole up to about 10% by weight of the particle growth inhibitor, for example from 0.5% up to about 10% by weight. The most useful range of particle growth inhibitor is up to about 6% by weight, for example from 1% to about 6%, or about 2.5% to about 6%, or about 3% to about 6% by weight of the particle growth inhibitor.

The surface area of the 1,4-diketopyrrolo[3,4-c]pyrrole product is directly related to the amount of the particle growth inhibitor present during the reaction and is inversely proportional to the particle size. Thus, the surface area of the product will increase as the amount of the particle growth inhibitor increases. In order for the 1,4-diketopyrrolo[3,4-c]pyrroles of formula (I) to be suitable for direct use as a pigment, the surface area of the reaction product should be at least 15 meters$^2$/gram, for example in the range of from about 15 to about 90 m$^2$/gram, preferably from about 20 to 90 m$^2$/gram, and most preferably from about 30 to about 70 m$^2$/gram. The surface area can be measured by nitrogen absorption or another suitable method.

In accordance with the invention, the reaction mixture contains an effective amount of the particle growth inhibitor. To be effective, the growth inhibitor is incorporated into the reaction mixture any time prior to the protolysis step. Preferably, the growth inhibitor is added to the reaction medium so that it is present during the reaction of the nitrile with the disuccinate. Addition of the growth inhibitor prior to or during the condensation results in smaller particle size pigments.

The process of the invention is preferably carried out in the temperature range of from about 60° to about 140° C., with the more preferred range being from about 80° to about 120° C.

The protolysis of the condensation product may be carried out with water, an alcohol containing 1 to 4 carbon atoms such as methanol or ethanol, or with an acid. It is preferred to use methanol, ethanol or cold water (0° to 25° C.). Examples of suitable acids are aliphatic or aromatic carboxylic or sulfonic acids, for example, formic acid, acetic acid, propionic add, oxalic acid, benzoic acid or benzenesulfonic acid. Further suitable acids are also mineral adds such as hydrochloric acid, sulfuric acid or phosphoric acid. When using an acid for quenching, it is preferred to use an organic acid, especially an aliphatic carboxylic acid such as acetic acid.

In the course of the protolysis, the compound of formula (I) precipitates and can be isolated by known methods, such as filtration.

For the reaction of the disuccinate with the nitrites of formula (II), (III), (XI) and (XII), it is possible to charge the reaction vessel, at low temperature, with all the components and then heat the mixture to the range of the reaction temperature, or to add the individual components, in any order, to each other in the range of the reaction temperature. A preferred embodiment is to charge the reaction vessel with the nitrile and the base and then adding the disuccinate in the range of the reaction temperature, which addition order has a particularly advantageous effect on the yield. Addition of the growth inhibitor prior to or during the condensation results in smaller particle size pigments. It is also possible to add the disuccinate and the nitrile simultaneously to the base. The process according to the invention may be carried out not only in a batchwise manner, but also continuously.

In particular, when using disuccinates containing alkyl radicals and alcoholates which are derived from lower alcohols such as methanol, ethanol, n-propanol, isopropanol or tert-butanol, it may be necessary to remove the lower alcohol formed during the reaction from the reaction medium continuously in order to obtain higher yields.

If an alcohol is used as solvent and an alcoholate as base, it may prove advantageous to choose an alcohol and alcoholate having the same alkyl moieties. It may likewise be advantageous if, in addition, the disuccinate also contains such alkyl groups.

The protolysis is preferably carried out in a temperature range of from about 0° to about 100° C., preferably from about 40° to about 80° C. To obtain a more transparent form of the pigment, the hydrolysis is preferably carried out at a lower temperature below 80° C. Conversely, a higher temperature may be utilized to obtain a more opaque form of the pigment.

The compounds of formula (I) are used as colorants for high molecular weight organic materials and can be used directly in the form in which they are obtained, i.e., without the need for particle-size reducing aftertreatments. The compounds of formula (I) are particularly suitable for certain end uses requiring a high degree of transparency such as in automotive coatings.

Depending on the end use, it may be advantageous to prepare mixtures of compounds of the formula (I). This can be done for example by mixing different reaction mixtures which have been prepared independently of one another before the protolysis, protolyzing them together and then isolating the resultant mixture of compounds of the formula (I). It is also possible to precipitate two or more compounds of the formula (I) together.

The instant invention further relates to a pigment composition comprising a pigmentary 1,4-diketopyrrolo-[3,4-c]pyrrole and an effective crystal growth inhibiting amount of a compound of formula (IV) to formula (X). The particle growth inhibitor is present in an amount of between 0.1 and 10 weight %, based on the weight of the diketopyrrolopyrrole. Although the particle growth inhibitor may be present in amounts greater than 10%, using more may adversely affect color. A more useful range of particle growth inhibitor is up to about 6% by weight, for example from 1% to about 6%, or about 2.5% to about 6%, or about 3% to about 6%, by weight of the particle growth inhibitor. The preferred embodiments described above apply here as well.

Organic materials of high molecular weight which may be pigmented with the compounds of formula (I) are for example cellulose ethers and esters such as ethyl cellulose, nitrocellulose, cellulose acetate or cellulose butylate, natural resins or synthetic resins such as polymerization resins or condensation resins, for example, aminoplasts, in particular urea/formaldehyde and melamine/formaldehyde resins, alkyd-resins, phenolic plastics, polycarbonates, polyolefins such as polystyrene, polyvinyl chloride, polyethylene, polypropylene, polyacrylonitrile, polyacrylates polyamides, polyurethanes or polyesters, rubber, casein, silicone and silicone resins, individually or in mixtures.

It is immaterial whether the above organic compounds of high molecular weight are in the form of plastics, melts or of spinning solutions, lacquers, paints or painting inks. Depending on the end use, it is advantageous to use the pigments of this invention in the form of toners or formulations. The high molecular weight organic compounds mentioned can be present individually or in mixtures. The compounds of the formula (I) are employed in an amount of about 0.01 to about 30%, preferably from about 0.1 to about 10%, by weight, based on the organic material of high molecular weight to be pigmented.

The colorations obtained, for example in plastics, filaments, lacquers or printing inks, have excellent tinctorial strength, good dispersibility, good fastness to oversprayings, migration, heat, light and atmospheric influences, as well as good gloss.

The high molecular weight organic substances are pigmented with the pigments of formula (I), for example, by mixing such a pigment, if desired, in the form of a masterbatch, into these substrates using roll mills and mixing or grinding apparatus. The pigmented material is then brought into the desired final form by known methods, such as calendaring, pressing, extruding, brushing, casting or injection molding. It may be desirable to incorporate plasticizers into the high molecular weight compounds before starting operation in order to produce non-rigid moldings or to reduce their brittleness. Suitable plasticizers are, for example, esters of phosphoric acid, phthalic acid or sebacic acid. Plasticizers can be incorporated before or after the incorporation of pigments according to the invention. To obtain different shades, it is further possible to add fillers or other coloring constituents, such as white, colored, or black pigments, in any desired amounts, to the high molecular weight organic substances, in addition to the pigments according to the invention.

The pigments prepared by the present process are particularly suitable for coloring polyvinyl chloride and polyolefins, such as polyethylene and polypropylene, and for pigmenting lacquers and paints, in particular metallic-effect-producing automotive topcoats. When used for this purpose, the pigments prepared in accordance with the present invention possess good general pigment properties such as high dispersability, high tinctorial strength and purity and high migration, heat, light and weathering fastness properties.

The following examples are for purposes of illustration, and are not intended to limit the scope of the present invention in any manner whatsoever. Parts and percentages are by weight unless otherwise specified.

EXAMPLES

Example 1

To a one liter four-necked round-bottomed flask, equipped with a stirrer, thermometer, reflux condenser with a drying tube, are added benzonitrile (25.8 g, 0.25 mole), tertiary-amyl alcohol (100 ml), potassium tertiary-butoxide (33.7 9, 0.3 mole) and 2-phthalimidomethyl quinacridone (0.576 g, 0.0012 mole), and the slurry is heated to 105° C. with moderate stirring. To this mixture is added dropwise a solution of diisopropyl succinate (20.2 g, 0.1 mole) in tertiary-amyl alcohol (20 ml) over a period of about 0.5 hours. After the addition is complete, the reaction mixture is maintained at 105° C. with stirring for 1.75 hours and then cooled to 50° C. To this mixture is added methanol (300 ml) and then water (80 ml). The reaction mass is heated under reflux for one hour, cooled to 50° C., filtered, washed with methanol followed by water and dried in an oven at 80° C. overnight, affording 20.3 g (70.5 % yield) of a solid pure yellow shade red pigment of the formula (XIII)

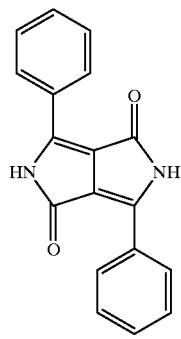

(XIII)

Comparative Example 1a

To a one liter four-necked round bottomed flask, equipped with a stirrer, thermometer reflux condenser with a drying tuber, are added benzonitrile (25.8 g, 0.25 mole), tertiary-amyl alcohol (100 ml) and potassium tertiary-butoxide (33.7 g, 0.3 mole), and the slurry is heated to 105° C. with moderate stirring. To this mixture is added dropwise a solution of diisopropyl succinate (20.2 g, 0.1 mole) in tertiary-amyl alcohol (20 ml) over a period of about 0.5 hours. After the addition is complete, the reaction mixture is maintained at 105° C. with stirring for 1.75 hours and then cooled to 50° C. To this mixture is added methanol (300 ml) and then water (80 ml). The reaction mass is heated under reflux for one hour, cooled to 50° C., filtered, washed with methanol followed by water and dried in an oven at 80° C. overnight to give 20.2 g (70% yield) of a pure yellow shade red pigment of the formula (XIII).

Samples from Example 1 and Comparative Example 1a are analyzed using X-ray diffraction. Their respective X-ray diffraction patterns indicate the same crystal phase for each sample but different particle sizes. X-ray diffraction indicates a smaller particle size for the pigment of Example 1 versus the pigment of Comparative Example 1 a, based on the peak heights, particularly the FWHM (Full Width at Half Max) of the peak at 6.6 two theta of 0.436 and 0.453, respectively. The smaller particle size of the pigment of Example 1 is also indicated by the rub out evaluation which shows the pigment of Example 1 to be of darker color than the pigment of Comparative Example 1a.

The foregoing Examples illustrate that the inclusion of the 2-phthalimidomethyl quinacridone inhibits the crystal growth of a diketopyrrolopyrrole pigment, resulting in a smaller sized particle pigment compared to a pigment prepared in the absence of the 2-phthalimidomethyl quinacridone.

Example 2

To a one-liter four-necked round-bottomed flask, equipped with a stirrer, thermometer, reflux condenser with a drying tube, are added p-chlorobenzonitrile (30.3 g, 0.22 mole), tert-amyl alcohol (130 ml), 2-phthalimidomethylquinacridone (0.72 9, 0.0015 mole) and potassium tert-butoxide (36.9 g, 0.33 mole), and the slurry is heated to about 95° C. with moderate stirring. To this mixture is added dropwise a solution of diisopropyl succinate (20.2 g, 0.1 mole) in tert-amyl alcohol (20 ml) over a period of about 0.5 hour. After complete addition, the reaction mixture is heated to reflux with stirring for 2 hours and then cooled to 50° C. To this mixture is added methanol (100 ml), followed by water (100 ml). The reaction mass is stirred for 0.25 hour, filtered, washed with 50% aqueous methanol and then water, and dried in an oven at 80° C. overnight, affording 31.4 g (88%) of a pure attractive red pigment of the formula (XIV)

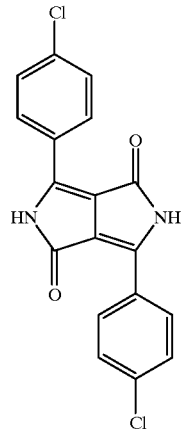

(XIV)

Comparative Example 2a

To a one-liter four-necked round-bottomed flask, equipped with a stirrer, thermometer, reflux condenser with a drying tube, are added p-chlorobenzonitrile (30.3 g, 0.22 mole), tert-amyl alcohol (130 ml) and potassium tert-butoxide (36.9 g, 0.33 mole), and the slurry is heated to about 95° C. with moderate stirring. To this mixture is added dropwise a solution of diisopropyl succinate (20.2 g, 0.1 mole) in tert-amyl alcohol (20 ml) over a period of about 0.5 hour. After complete addition, the reaction mixture is heated to reflux with stirring for 2 hours and then cooled to 50° C. To this mixture is added methanol (100 ml), followed by water (100 ml). The reaction mass is stirred for 0.25 hour, filtered, washed with 50% aqueous methanol and then water, and dried at 80° C. overnight to give 31.4 g of a pure opaque red pigment of the formula (XIV).

The pigments of Example 2 and Comparative Example 2a are analyzed using X-ray diffraction, which indicates that the pigment of Example 2 is smaller in particle size than the pigment of Comparative Example 2a. The smaller particle size of the pigment of Example 2 is also indicated by the rub out evaluation which shows a darker masstone as compared to the pigment of Comparative Example 2a.

Example 3

To a one-liter four-necked round-bottomed flask, equipped with a stirrer, thermometer, reflux condenser with drying tube, are added p-chlorobenzonitrile (30.3 9, 0.22 mole), tert-amyl alcohol (130 ml) and potassium tert-butoxide (36.9 9, 0.33 mole), and the slurry is heated to about 95° C. with moderate stirring. To this mixture is added dropwise a solution of diisopropyl succinate (20.2 9, 0.1 mole) in tert-amyl alcohol (20 ml) over a period of about 0.5 hour. After complete addition, the reaction mass is heated to reflux, with stirring for 2 hours and then cooled to 50° C. To this mixture is added 2-phthalimidomethyl quinacridone (0.72 g, 0.0015 mole), methanol (100 ml) and water (100 ml). The reaction mass is stirred for 0.25 hour, filtered, washed with 50% aqueous methanol and then water, and dried at 80° C. in an oven overnight, affording 31.3 g of a pure attractive red pigment of the formula (XIV).

The pigment is analyzed using X-ray diffraction, which indicates that the pigment of this Example is smaller in particle size than the pigment of Comparative Example 2a, but slightly larger than the pigment of Example 2. The rub out evaluation shows the pigment of this Example to be darker in masstone as compared to the pigment of Comparative Example 2a, but slightly lighter than the pigment of Example 2.

The foregoing illustrates that while addition of the growth inhibitor just before the protolysis step results in substantial crystal growth inhibition, it is more beneficial to include the growth inhibitor during the synthesis to obtain a pigment of an even smaller particle size.

Example 4

The same procedure as in Example 2 is followed, except using a different amount of the 2-phthalimidomethyl quinacridone (1.21 g, 0.0026 mole) to yield 31.4 g of an attractive deep red colored pigment of formula (XIV).

The pigment is analyzed using X-ray diffraction, which shows the pigment of this Example to be significantly smaller in particle size as compared to the pigment of Example 2. Rub out evaluation shows the pigment of this Example to be extremely dark.

The foregoing illustrates that the particle size of the pigment is directly associated with the amount of the growth inhibitor which is added. Significant crystal growth inhibition is achieved by adding increasing amounts of the growth inhibitor.

Example 5

To a one-liter four-necked round-bottomed flask, equipped with a stirrer, thermometer, reflux condenser with a drying tube are added 4-phenylbenzylnitrile (35.4 g, 0.20 mole), tert-amyl alcohol (130 ml), 2-phthalimidomethyl quinacridone (0.8 g, 0.0017 mole) and potassium tert-butoxide (36.9 9, 0.33 mole), and the slurry is heated to about 90° C. with moderate stirring. To this mixture is added dropwise a solution of diisopropyl succinate (20.2 g, 0.1 mole) in tert-amyl alcohol (20 ml) over a period of about 0.5 hour. After complete addition, the reaction mixture is heated to reflux with stirring for 2 hours and then cooled to 50° C. To this mixture is added methanol (100 ml) and then water (100 ml). The reaction mass is stirred for 0.25 hour, washed with 50% aqueous methanol followed by water, and dried at 80° C. in an oven overnight to yield 30.8 g (70%) of a pure blue shade red pigment of the formula (XV)

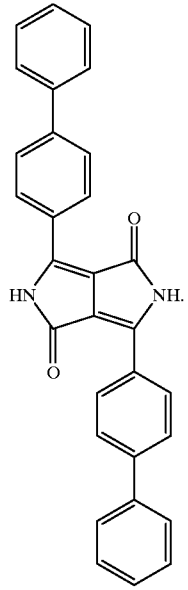

(XV)

Comparative Example 5

The same procedure of Example 5 is followed, except omitting inclusion of the 2-phthalimidomethyl quinacridone, to obtain a pigment of formula (XV).

The pigments of Example 5 and Comparative Example 5a are analyzed using X-ray diffraction, which indicates that the pigment of Example 5 has a smaller particle size than that of the pigment of Comparative Example 5a. Rub out evaluation shows a darker masstone for the pigment of Example 5 as compared to that of Comparative Example 5a.

Example 6

The procedure of Example 5 is followed, except using a different amount of the 2-phthalimidomethyl quinacridone (1.58g, 0.0034 mole), to obtain 30.9 g of an attractive blue shade red pigment of the formula (XV).

The pigment of this Example is analyzed using X-ray diffraction, which shows a significantly smaller particle size as compared to the particle size of the pigment of Example 5. The rub out evaluation indicates an extremely dark pigment.

The foregoing illustrates that the particle size of the pigment is directly associated with the amount of the growth inhibitor which is added. Significant crystal growth inhibition is achieved by adding increasing amounts of the growth inhibitor.

Example 7

The procedure of Example 2 is followed, except using pyrazolyl-2-methylquinacridone (1.1 g, 0.0027 mole) as the particle growth inhibitor, to obtain 31.4 g of a dark red pigment of the formula (XIV).

The pigment of this Example is analyzed using X-ray diffraction, which indicates a significantly smaller particle size as compared to that of the pigment of Example 2. The rub out evaluation shows the pigment to be very dark in masstone.

Example 8

The procedure of Example 2 is followed, except using aluminum quinacridone sulfonate (1.1 g, 0.0027 mole) as the particle growth inhibitor, to obtain 31.5 g of a very dark red pigment of formula (XIV).

The pigment of this Example is analyzed using X-ray diffraction, which indicates a particle size comparable to that of Example 7, but a significantly smaller particle size than that of the pigment of Example 2. The rub out evaluation shows the pigment to be very dark in masstone, similar to that of Example 7.

Example 9

The procedure of Example 2 is followed, except using monochlorodiketopryrrolopyrrole sulfonic acid (1.1 g, 0.0027 mole) as the particle growth inhibitor, to obtain 31.4 g of a dark red pigment of the formula (XIV).

The pigment of this Example is analyzed using X-ray diffraction, which indicates a particle size comparable to that of Examples 7 and 8, but a significantly smaller particle size than that of Example 2. The rub out evaluation shows the pigment to be very dark in masstone, similar to that of Examples 7 and 8.

Examples 10–23

The general procedure of any of Examples 1–9 is followed, using any appropriate particle growth inhibitor in accordance with the instant process and using a nitrile of the formula R—CN, to obtain a pigment of the formula

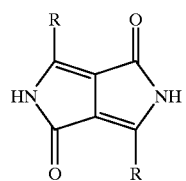

in a yield similar to and having a particle size similar to that of the preceding Examples, wherein R is as defined in Table I.

TABLE I

| Example | R |
|---|---|
| 10 | H₃C—⌬— |
| 11 | ⌬(Cl)— |
| 12 | CH₃OOC—⌬— |
| 13 | ⌬(NC)— |
| 14 | NC—⌬— |
| 15 | pyridin-2-yl |
| 16 | pyridin-3-yl |
| 17 | pyridin-4-yl |
| 18 | naphthalen-1-yl |
| 19 | naphthalen-2-yl |
| 20 | (H₃C)₂N—⌬— |
| 21 | ⌬(CH₃)— |
| 22 | ⌬(Cl,Cl)— |
| 23 | t-butyl—⌬— |

Examples 24–48

The general procedure of any of Examples 1–9 is followed, using any appropriate particle growth inhibitor in accordance with the instant process and using a nitrile of the formula R'—CN or R"—CN wherein R' and R" are identical and are as defined in Table II (Examples 24–33) or using appropriate equimolar amounts of the nitrile of the formula R'—CN and the nitrile R"—CN, wherein R' and R" are different and are as defined as in Table III (Examples 34–48), to obtain a pigment of the formula

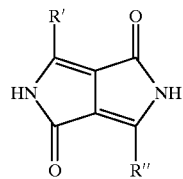

in a yield similar to and having a particle size similar to that of the preceding Examples.

TABLE II

| Example | R'=R" |
|---|---|
| 24 | 3-(trifluoromethyl)phenyl |
| 25 | 6-pentyloxypyridin-3-yl |
| 26 | 4-(trifluoromethyl)phenyl |
| 27 | 4'-cyanobiphenyl-4-yl |
| 28 | 4-tert-butylphenyl |
| 29 | 3,4-dimethylphenyl |
| 30 | furan-2-yl |
| 31 | 4-methylphenyl |
| 32 | thiophen-2-yl |

TABLE II-continued

| Example | R'=R" |
|---|---|
| 33 | 3,5-dichlorophenyl |

TABLE III

| Example | R' | R" |
|---|---|---|
| 34 | phenyl | 4-chlorophenyl |
| 35 | phenyl | 4-cyanophenyl |
| 36 | phenyl | pyridin-4-yl |
| 37 | phenyl | pyridin-3-yl |
| 38 | phenyl | 4-methylphenyl |
| 39 | 4-chlorophenyl | pyridin-4-yl |
| 40 | phenyl | 4-methoxyphenyl |
| 41 | 4-chlorophenyl | pyridin-3-yl |
| 42 | 4-chlorophenyl | 3-chlorophenyl |
| 43 | 4-chlorophenyl | 4-methoxyphenyl |

TABLE III-continued

| Example | R' | R" |
|---|---|---|
| 44 | H₃C—⟨benzene⟩— | H₃CO—⟨benzene⟩— |
| 45 | H₃C—⟨benzene⟩— | Cl—⟨benzene⟩— |
| 46 | ⟨benzene-3-CH₃⟩— | ⟨benzene⟩— |
| 47 | ⟨3,4-diCl-benzene⟩— | CH₃—⟨benzene⟩— |
| 48 | t-butyl—⟨benzene⟩— | ⟨benzene⟩— |

Examples 49–63

The same general procedure of any of Examples 1–9 is repeated, using any appropriate nitrile or mixtures thereof and any appropriate disuccinate in accordance with the instant process, and using the particle growth inhibitor as defined in Table IV.

TABLE IV

| Example | Growth Inhibitor |
|---|---|
| 49 | imidazol-1-ylmethylquinacridone |
| 50 | imidazole-1-ylmethyldiketopyrrolopyrrole |
| 51 | pyrazol-1-ylmethylquinacridone |
| 52 | pyrazol-1-ylmethyldiketopyrrolopyrrole |
| 53 | phthalimidomethyldiketopyrrolopyrrole |
| 54 | quinacridone monosulfonic acid |
| 55 | diketopyrrolopyrrole monosulfonic acid |
| 56 | sodium diketopyrrolopyrrole monosulfonate |
| 57 | potassium diketopyrrolopyrrole monosulfonate |
| 58 | magnesium diketopyrrolopyrrole monosulfonate |
| 59 | calcium diketopyrrolopyrrole monosulfonate |
| 60 | strontium diketopyrrolopyrrole monosulfonate |
| 61 | dimethylaminopropylquinacridone monosulfoamide |
| 62 | dimethylaminopropylquinacridone disulfoamide |
| 63 | imidazol-2-ylmethylquinacridone |

What is claimed is:

1. A process for the direct preparation of a pigmentary 1,4-diketopyrrolo[3,4-c]pyrrole of the formula (I)

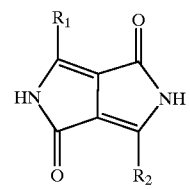

(I)

wherein each of $R_1$ and $R_2$ independently of the other is an isocyclic or heterocyclic aromatic radical, which process comprises heating an appropriate molar ratio of a disuccinate with a nitrile of the formula (II)

(II)

$R_1$—CN or of the formula (III)

(III)

$R_2$—CN or with mixtures of said nitrites, in an organic solvent and in the presence of a strong base and an effective amount of a particle growth inhibitor, to form an intermediate condensation product, and protolyzing said intermediate condensation product to form the compound of formula (I), wherein said particle growth inhibitor is a compound of formula (IV)

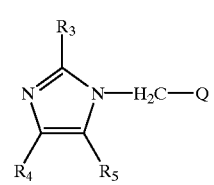

(IV)

wherein $R_3$, $R_4$ and $R_5$ are, each independently of the other, hydrogen, chlorine, bromine, fluorine, $C_1$–$C_6$alkyl, $C_1$–$C_6$alkoxy or an isocyclic or heterocyclic aromatic radical and Q is a quinacridone or diketopyrrolopyrrole moiety;

a compound of formula (V)

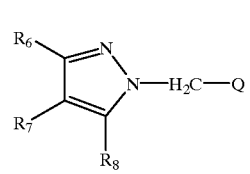

(V)

wherein $R_6$, $R_7$ and $R_8$ are, each independently of the other, hydrogen, chlorine, bromine, fluorine, $C_1-C_6$alkyl, $C_1-C_6$alkoxy or an isocyclic or heterocyclic aromatic radical and Q is as defined above;

a compound of formula (VI)

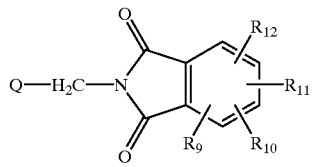
(VI)

wherein $R_9$, $R_{10}$, $R_{11}$ and $R_{12}$ are, each independently of the other, hydrogen, chlorine, bromine, fluorine, $C_1-C_6$alkyl, $C_1-C_6$alkoxy or an isocyclic or heterocyclic aromatic radical and Q is as defined above;

a compound of formula (VII)

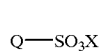
(VII)

wherein X is hydrogen, sodium, potassium, magnesium, calcium, strontium or aluminum and Q is as defined above;

a compound of formula (VIII)

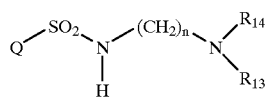
(VIII)

wherein n is an integer from 2 to 4; $R_{13}$ and $R_{14}$ are, each independently of the other, $C_1-C_6$alkyl or together with the nitrogen atom to which they are bonded form a 5- or 6-membered heterocyclic ring; and Q is as defined above;

a compound of formula (IX)

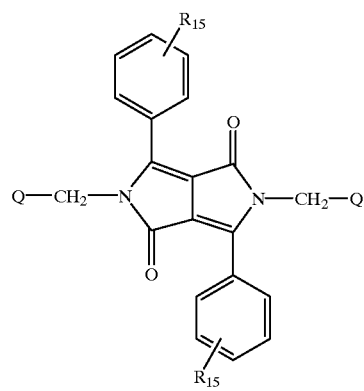
(IX)

wherein $R_{15}$ is hydrogen, chlorine, bromine, fluorine, $C_1-C_6$alkyl, $C_1-C_6$alkoxy, phenyl, di-$C_1-C_6$alkylamino, $C_1-C_6$alkylthio, phenylthio or phenoxy, and Q is as defined above; wherein said compound is substituted by from 0 to 6 moles of —SO3M per mole of said compound, wherein M is hydrogen or a metal or ammonium cation;

or a compound of the formula (X)

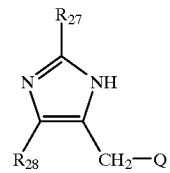
(X)

wherein $R_{27}$ and $R_{28}$ are, each independently of the other, hydrogen, chlorine, bromine, fluorine, $C_1-C_6$alkyl, $C_1-C_6$alkoxy or an isocyclic or heterocyclic aromatic radical and Q is as defined above.

2. A process according to claim 1, wherein only one nitrile of formula (II) or of formula (III) is used.

3. A process according to claim 1 where, in the formula (I), $R_1$ and $R_2$ are, each independently of the other, unsubstituted phenyl or naphthyl or which phenyl or naphthyl contain non-watersolubilising substituents.

4. A process according to claim 1 wherein $R_1$ and $R_2$, each independently of the other, are phenyl or said phenyl substituted by one or two chlorine atoms, by one or two methyl groups, by methoxy, by trifluoromethyl, by cyano, by methoxycarbonyl, by methyl, by tert-butyl, by dimethylamino or by cyanophenyl; naphthyl, biphenylyl; pyridyl or said pyridyl substituted by amyloxy; furyl or thienyl.

5. A process according to claim 4 wherein $R_1$ and $R_2$, each independently of the other is phenyl, 3-chlorophenyl, 4-chlorophenyl, 3,5-dichlorophenyl, 4-methylphenyl, 4-methoxyphenyl, 3-trifluoromethylphenyl, 4-trifluoromethylphenyl, 3-cyanophenyl, 4-cyanophenyl, 4-methoxycarbonylphenyl, 4-methylphenyl, 4-tert-butylphenyl, 4-dimethylaminophenyl, 4-(para-cyanophenyl) phenyl, 1-naphthyl, 2-naphthyl, 4-biphenylyl, 2-pyridyl, 6-amyloxy-3-pyridyl, 2-furyl or 2-thienyl.

6. A process according to claim 5 where $R_1$ and $R_2$ each independently of the other, is phenyl, 4-chlorophenyl, 4-methylphenyl, 4-tert-butylphenyl, 4-biphenylyl, or 3-cyanophenyl.

7. A process according to claim 1 where the nitrile of formula (II) or of formula (III) is of the formula (XI)

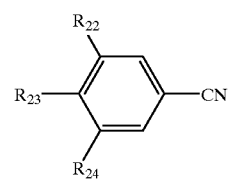
(XI)

wherein each of $R_{22}$, $R_{23}$ and $R_{24}$, independently of one another, is hydrogen, fluorine, chlorine, bromine, carbamoyl, cyano, trifluoromethyl, $C_2-C_{13}$alkylcarbamoyl, $C_1-C_{12}$alkyl, $C_1-C_{12}$alkoxy, $C_1-C_{12}$alkylmercapto, $C_2-C_{13}$alkoxycarbonyl, $C_2-C_{13}$alkanoylamino, $C_1-C_{12}$ monoalkylamino, $C_2-C_{24}$dialkylamino, phenyl or phenoxy, phenylmercapto, phenoxycarbonyl, phenylcarbamoyl or benzoylamino, each unsubstituted or substituted by halogen, $C_1-C_{12}$alkyl or $C_1-C_{12}$alkoxy, with the proviso that at least one of $R_{22}$, $R_{23}$ or $R_{24}$ is hydrogen.

8. A process according to claim 1 where the nitrile of formula (II) or of formula (III) is of the formula (XII)

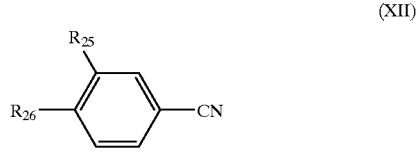

(XII)

wherein both $R_{25}$ and $R_{26}$ are hydrogen, or one of $R_{25}$ or $R_{26}$ is chlorine, bromine, $C_1$–$C_4$alkyl, cyano, $C_1$–$C_4$alkoxy, or is phenyl, phenoxy, carbamoyl or $C_2$–$C_5$alkylcarbamoyl, each unsubstituted or substituted by chlorine or methyl, or is phenylcarbamoyl which is unsubstituted or substituted by chlorine, methyl or methoxy, and the other is hydrogen.

9. A process according to claim 1, wherein the disuccinate is a symmetrical dialkyl succinate containing from 1 to 18 carbon atoms in each moiety.

10. A process according to claim 1 wherein the disuccinate is a symmetrical dialkyl succinate, wherein alkyl is sec- or tert-alkyl.

11. A process according to claim 1 wherein the disuccinate is diisopropyl succinate.

12. A process according to claim 1 wherein the solvent is a secondary or tertiary alcohol.

13. A process according to claim 1 wherein the strong base is an alkali metal alcoholate.

14. A process according to claim 13 wherein the alkali is sodium or potassium.

15. A process according to claim 13 wherein the alkali metal alcoholate is derived from a secondary or tertiary alcohol.

16. A process according to claim 1 where the particle growth inhibitor is a compound of formula (IV) wherein $R_3$, $R_4$ and $R_5$ are, each independently of the other, hydrogen or methyl.

17. A process according to claim 1 where the particle growth inhibitor is a compound of formula (V) wherein $R_6$, $R_7$ and $R_8$ are, each independently of the other, hydrogen or methyl.

18. A process according to claim 1 where the particle growth inhibitor is a compound of formula (VI) wherein $R_9$, $R_{10}$, $R_{11}$ and $R_{12}$ are, each independently of the other, hydrogen, methyl or chlorine.

19. A process according to claim 1 where the particle growth inhibitor is a compound of formula (VII) wherein Q is an unsubstituted quinacridone or diketopyrrolopyrrole moiety and X is hydrogen, calcium, magnesium, aluminum or strontium.

20. A process according to claim 1 where the particle growth inhibitor is a compound of formula (VIII) wherein n is 2 or 3 and $R_{13}$ and $R_{14}$ are methyl.

21. A process according to claim 1 where the particle growth inhibitor is a compound of formula (IX) wherein Q is an unsubstituted quinacridone moiety or a 4,11-dichloroquinacridone or 4,11-dimethylquinacidone moiety.

22. A process according to claim 1 where the particle growth inhibitor is a compound of formula (IX) wherein Q is an unsubstituted diketopyrrolopyrrole moiety or a di-methyldiketopyrrolopyrrole or di-tert-butyldiketopyrrolopyrrole moiety.

23. A process according to claim 1 where the particle growth inhibitor is a compound of formula (IX) wherein $R_{15}$ is hydrogen, methyl, tert-butyl or chlorine.

24. A process according to claim 1 where the particle growth inhibitor is a compound of formula (IX) wherein $R_{15}$ is located in the 4-position on the phenyl ring.

25. A process according to claim 1 where the particle growth inhibitor is a compound of formula (X) wherein $R_{27}$ and $R_{28}$ are, each independently of the other, hydrogen or methyl.

* * * * *